US008394142B2

(12) United States Patent
Bertagnoli et al.

(10) Patent No.: US 8,394,142 B2
(45) Date of Patent: Mar. 12, 2013

(54) CUSTOMIZING AN INTERVERTEBRAL IMPLANT

(75) Inventors: Rudolph Bertagnoli, Vienna (AT); Thierry Marnay, Catelnau le Lez (FR); Christophe Geisert, Huffingen (DE); Eduard Kufeld, Tuttlingen (DE); Barbara Schweizer, Sulz am Neckar (DE)

(73) Assignee: Synthes USA, LLC, West Chester, PA (US)

( * ) Notice: Subject to any disclaimer, the term of this patent is extended or adjusted under 35 U.S.C. 154(b) by 657 days.

(21) Appl. No.: 11/150,468

(22) Filed: Jun. 13, 2005

(65) Prior Publication Data
US 2006/0282020 A1 Dec. 14, 2006

(51) Int. Cl.
*A61F 2/44* (2006.01)
(52) U.S. Cl. .................................... 623/17.11
(58) Field of Classification Search ............... 623/16.11, 623/17.11–17.16; D24/155; 128/898
See application file for complete search history.

(56) References Cited

U.S. PATENT DOCUMENTS

| | | | |
|---|---|---|---|
| 4,109,383 A | 8/1978 | Reed et al. | |
| 4,575,805 A | 3/1986 | Moermann et al. | |
| 4,936,862 A * | 6/1990 | Walker et al. | 128/898 |
| 5,147,404 A | 9/1992 | Downey | |
| 5,261,913 A | 11/1993 | Marnay | |
| 5,314,477 A | 5/1994 | Marnay | |
| 5,514,180 A | 5/1996 | Heggeness et al. | |
| 5,527,315 A | 6/1996 | Jeanson et al. | |
| 5,658,285 A | 8/1997 | Marnay et al. | |
| 5,723,013 A | 3/1998 | Jeanson et al. | |
| 5,741,215 A | 4/1998 | D'Urso | |
| 5,798,924 A * | 8/1998 | Eufinger et al. | 700/117 |
| 5,824,085 A * | 10/1998 | Sahay et al. | 128/898 |

(Continued)

FOREIGN PATENT DOCUMENTS
DE 197 47 979 5/1999
DE 19922279 A1 * 11/2000
(Continued)

OTHER PUBLICATIONS

Cranin AN, et al; An in vitro comparison of the computerized tomography/CAD-CAM and direct bone impression techniques for subperiosteal implant model generation; J Oral Implantol. 1998; 24(2):74-9.

(Continued)

*Primary Examiner* — Alvin Stewart
*Assistant Examiner* — Tara Carter
(74) *Attorney, Agent, or Firm* — Woodcock Washburn LLP

(57) ABSTRACT

A method and apparatus for customizing an intervertebral implant includes the initial step of obtaining a 3D anatomy of a series of vertebrae including an abnormal vertebra in a computer. The 3D anatomy of the series is then repositioned in the computer to eliminate the deformity caused by the abnormal vertebra. It is next determined whether a superior or inferior surface of the abnormal vertebra is an abnormal surface which causes the deformity, whereby an approximate gap between the abnormal surface and a desired normal surface is determined. Using that gap determination, a custom implant is constructed to engage the abnormal surface and fill the determined gap. Thus, when the implant is implanted between the abnormal surface and an adjacent surface of an adjacent vertebrae, the deformity is substantially compensated for. The implant may have articulation between the endplates to allow relative movement therebetween.

21 Claims, 3 Drawing Sheets

U.S. PATENT DOCUMENTS

| | | | |
|---|---|---|---|
| 5,865,846 A * | 2/1999 | Bryan et al. | 128/898 |
| 5,895,428 A | 4/1999 | Berry | |
| 6,254,639 B1 * | 7/2001 | Peckitt | 623/11.11 |
| 6,470,207 B1 | 10/2002 | Simon et al. | |
| 6,503,279 B1 | 1/2003 | Webb et al. | |
| 6,510,334 B1 * | 1/2003 | Schuster et al. | 600/407 |
| 6,849,223 B2 | 2/2005 | Dean et al. | |
| 6,896,701 B2 | 5/2005 | Boyd et al. | |
| 6,932,842 B1 * | 8/2005 | Litschko et al. | 623/16.11 |
| 2004/0117022 A1 | 6/2004 | Marnay et al. | |
| 2004/0215198 A1 | 10/2004 | Marnay et al. | |
| 2004/0225362 A1 | 11/2004 | Richelsoph | |
| 2005/0021042 A1 | 1/2005 | Marnay et al. | |
| 2005/0022098 A1 * | 1/2005 | Vayanos et al. | 714/776 |
| 2005/0027362 A1 | 2/2005 | Williams et al. | |
| 2005/0043799 A1 | 2/2005 | Reiley | |
| 2005/0043835 A1 | 2/2005 | Christensen | |
| 2005/0049707 A1 | 3/2005 | Ferree | |
| 2005/0055029 A1 * | 3/2005 | Marik et al. | 606/87 |
| 2005/0055098 A1 * | 3/2005 | Zdeblick et al. | 623/17.11 |
| 2005/0060034 A1 | 3/2005 | Berry et al. | |
| 2005/0085917 A1 | 4/2005 | Marnay et al. | |

FOREIGN PATENT DOCUMENTS

| | | |
|---|---|---|
| WO | WO-01/19295 | 3/2001 |
| WO | WO-2004/110309 | 12/2004 |

OTHER PUBLICATIONS

Dean D, et al; Computer aided design of large-format prefabricated cranial plates; J Craniofac Surg. Nov. 2003; 14(6):819-32.

Eppley BL, et al; Computer-generated patient models for reconstruction of cranial and facial deformities; J Craniofac Surg. Nov. 1998; 9(6):548-56.

Eufiner H, et al; Computer-assisted prefabrication of individual craniofacial implants; AORN J. Nov. 2001; 74(5):648-54; quiz 655-6, 658-62.

Eufinger H, et al; Experimental computer-assisted alloplastic sandwich augmentation of the atrophic mandible; J Oral Maxillofac Surg. Dec. 1999; 57(12):1436-40; discussion 1440-1.

Eufinger H, et al; Individual prefabricated titanium implants in reconstructive craniofacial surgery: clinical and technical aspects of the first 22 cases; Plast Reconstr Surg. Aug. 1998; 202(2):300-8.

Eufinger H, et al; Prefabricated prostheses for the reconstruction of skull defects; Int J Oral Maxillofac Surg. Feb. 1995; 24(1 Pt 2):104-10.

Eufinger H, et al; Reconstruction of craniofacial bone defects with individual alloplastic implants based on CAD/CAM-manipulated CT-data; J Craniomaxillofac Surg. Jun. 1995; 23(3):175-81.

Eufinger H, et al; Single-step fronto-orbital resection and reconstruction with individual resection template and corresponding titanium implant: a new method of computer-aided surgery; J Craniomaxillofac Surg. Dec. 1998; 26(6):373-8.

Gulyas G, et al; Cranioplasty using computer-designed implants (preliminary report); Orv Hetil. Oct. 29, 1995; 136(44):2393-7.

Klein HM, et al; Stereolithographic model construction based on 3-dimensional reconstructed CT sectional image sequences; Rofo. May 1992; 156(5):429-32.

Langlotz F, et al; A pilot study on computer-assisted optimal contouring of orthopedic fixation devices; Comput Aided Surg. 1999; 4(6):305-13.

Lo LJ, et al; Computer-aided reconstruction of traumatic fronto-orbital osseous defects: aesthetic considerations; Chang Gung Med J. Apr. 2004; 27(4):283-91.

Lopponen H, et al; Computed tomography data based rapid prototyping model of the temporal bone before cochlear implant surgery; Acta Otolaryngol Suppl. 1997; 529:47-9.

Redl P, et al; Computer tomography in implantology; Fogorv Sz. May 1995; 88(5):169-72.

Schlieper J, et al; CT-computer-template-assisted planning of implant and magnet position in epi-prosthetic management of facial defects; Mund Kiefer Gesichtschir. Jan. 2001; 5(1):22-7.

Stojadinovic S, et al; One-step resection and reconstruction of the mandible using computer-aided techniques—experimental and clinical results; Mund Kiefer Gesichtschir. May 1999; 3 Suppl 1:S151-3.

Synthes Brochure, PSI Patient Specific Implants Derived from CT data for excellent reconstructive results, 2004.

Tal H, et al; A comparison of panoramic radiography with computer tomography in the planning of implant surgery; Dentomaxillofac Radiol. Feb. 1991; 20(1):40-2.

Teng Y, et al; Fabrication of custom-made artificial semi-knee joint based on rapid prototyping technique: three-dimensional reconstruction of femoral condyle; Zhongguo Xiu Fu Chong Jian Wai Ke Za Zhi. Jul. 2004; 18(4):257-60.

Truitt HP, et al; Morphologic replication of the mandible using a computerized tomography for the fabrication of a subperiosteal implant; Oral Surg Med Oral Pathol. May 1988; 65(5):499-504.

Van Steenberghe D, et al; Bone augmentation by means of a stiff occlusive titanium barrier; Clin. Oral Implants Res. Feb. 2003; 14(1):63-71.

Weihe S, et al: Synthesis of CAD/CAM, robotics and biomaterial implant fabrication: single-step reconstruction in computer-aided frontotemporal bone resection; Int J Oral Maxillofac Surg. Oct. 2000; 29(5):384-8.

Wurm G, et al; Prospective study on cranioplasty with individual carbon fiber reinforced polymer (CFRP) implants produced by means of stereolithography; Surg Neurol. Dec. 2004; 62(6):510-21.

* cited by examiner

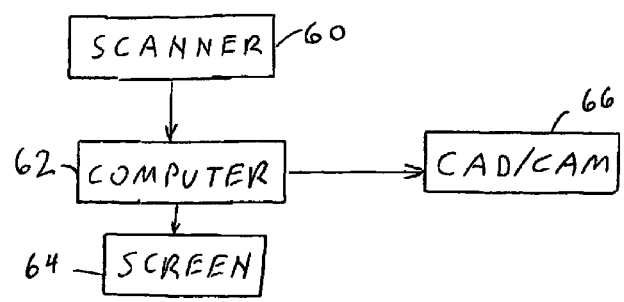
FIG. 7
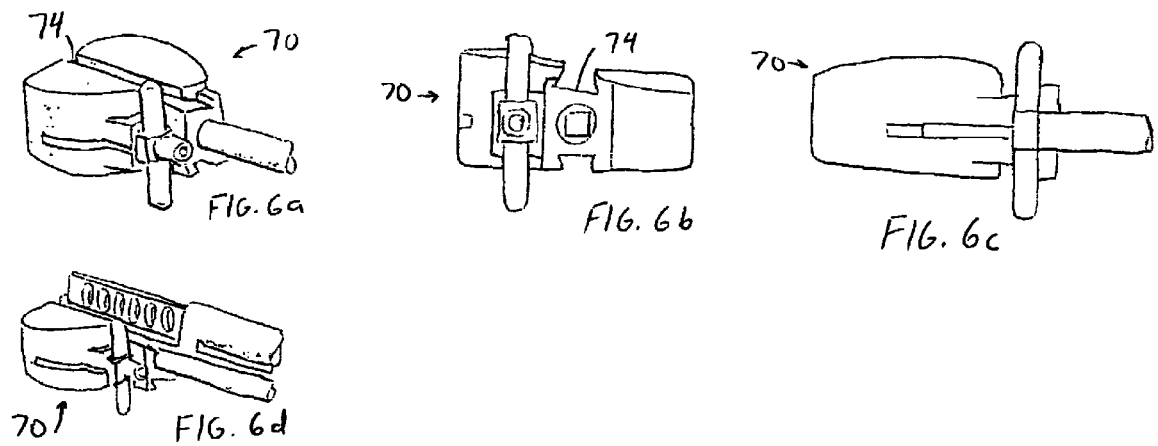
FIG. 6a   FIG. 6b   FIG. 6c
FIG. 6d

CUSTOMIZING AN INTERVERTEBRAL IMPLANT

FIELD OF THE INVENTION

The invention relates to intervertebral implants, and an particular it relates to a customized intervertebral implant and a method of providing same.

BACKGROUND OF THE INVENTION

Patients with a broken vertebra and/or degenerative disc disease often have a deformed spine caused by trauma or the like due to a collapsed vertebra. The deformed spine results in a scoliotic or kyphotic spine. The usual treatment for such a condition where the adjacent vertebrae are collapsed is a fusion of the vertebrae concerned. With fusion, after accompanying repositioning of the spine during surgery, the deformed spine is returned to its desired anatomical shape. However, after fusion the adjacent levels of the spine experience increased movement as the adjacent levels must compensate for the immobility of the fused vertebrae. This results in higher strains for the adjacent levels and discs, leading to more disc disease problems and back pain.

While various artificial vertebrae have been proposed in the prior art to serve as a replacement for a damaged vertebra, and thus to help avoid the problems associated with fusion, this requires removal of the damaged vertebra. An example of such a replacement vertebra is shown in US Published Application 2005/0060034 to Berry et al.

Another major improvement in the treatment of the spine are intervertebral implants of the type which provide articulation such as universal movement between upper and lower endplates thereof, and hence between adjacent vertebrae. Examples of such intervertebral implants are those disclosed in US Published Applications 2005/0085917 (Marnay et al.) and 2004/0117022 (Marnay et al.); and examples of exemplary tools and methods for insertion of such intervertebral implants are those disclosed in International Published Application No. WO01/19295 (Beyersdorf et al.) and in US Published Applications 2004/0215198 (Marnay et al.), 2005/0021042 (Marnay et al), and 2004/0117022 (Marnay et al.). The disclosures of these published applications are hereby incorporated by reference. However, such intervertebral implants are not currently adaptable for use with broken or damaged vertebrae.

Besides trauma or the like which results in a deformity, natural miss-shaping of vertebrae may also result in a deformity or undesired curvature of the spine. Typical of such conditions are scoliosis or kyphosis.

BRIEF SUMMARY OF THE INVENTION

In accordance with the present invention, a method for customizing an intervertebral implant is provided, wherein the intervertebral implant is implanted in an intervertebral space within a series of vertebrae because the series of vertebrae have a deformity. The deformity may result from trauma which results in a resultant damaged vertebra, or by malformation during growth. For convenience, hereafter such a damaged or malformed vertebra will be referred to as "abnormal".

Also for convenience, the series of vertebra is considered to include an abnormal vertebra which is the cause of the deformity, a vertebra superior to the abnormal vertebra, and a vertebra inferior to the abnormal vertebrae. The customized intervertebral implant then replaces the disc between the abnormal surface of the abnormal vertebra and the surface adjacent to the abnormal surface of the adjacent vertebra, so that the abnormal vertebra is retained (not removed).

A particular advantage of the present invention is to provide a customized intervertebral implant wherein the implant is of the type described above having opposed endplates which are articulated so as to provide movement such as universal movement therebetween and hence between the adjacent vertebrae.

The method comprises the initial step of obtaining a 3D anatomy of the series of vertebrae in a computer. Next, a repositioning of the 3D anatomy of each vertebra of the series is made in the computer to eliminate as far as possible the deformity of the series. It is then determined whether a superior or inferior surface of the abnormal vertebra is an abnormal surface which causes the deformity of the series. In addition, an approximate gap between the abnormal surface of the abnormal vertebra and a desired normal or desired surface of the abnormal vertebra is also determined. Using that determination of the gap, a custom implant is constructed which will engage the abnormal surface and fill the determined gap. In this manner, when the implant is implanted between the abnormal surface of the abnormal vertebrae and an adjacent surface of an adjacent vertebrae of the series, the deformity is substantially or desirably compensated for.

In a preferred embodiment of the present invention, the constructing step includes constructing an adjacent surface of the implant with a height which will engage the abnormal surface and fill the determined gap. When the surface of the implant is so customized, preferably the abnormal surface is smoothed in the computer so that the custom surface of the implant is matched to the smoothed surface. Conveniently, the constructing step further includes the step of transferring data from the computer to a CAD/CAM milling machine which makes the custom surface.

In a preferred arrangement, wherein the implant is of the type having opposed endplates with articulation for relative movement therebetween and an inlay received in one of the endplates, the constructing step includes the constructing of the inlay with a varying height which will cause a surface of the endplate adjacent the abnormal surface to fill the determined gap. In this embodiment, the constructing step includes the step of smoothing of the abnormal surface in the computer so that the varied height of the inlay is matched to the gap of the smoothed surface. Further, the constructing step includes the step of transferring data from the computer to a CAD/CAM milling machine which makes the varying height inlay.

The present invention also includes a method for providing a custom designed intervertebral implant for insertion into an irregularly shaped intervertebral space, where the space is bounded on one side by an abnormal vertebra. This method comprises the steps of determining a shape of the irregular intervertebral space, custom designing an implant to match opposing vertebral surfaces of the intervertebral space, and then inserting the custom designed implant into the intervertebral space such that the custom designed implant essentially fills the intervertebral space.

Preferably, the custom designed implant is of the type wherein the endplates have articulation for relative movement therebetween. In addition, where the custom designed implant has keels, the invention further includes the step of forming a trial implant to assist in forming grooves for the keels in the adjacent vertebra.

The present invention further includes a method of providing a customized implant of the type having opposed endplates with articulation for relative movement therebetween.

This method comprises the steps of determining the shape of an intervertebral space between adjacent vertebrae, shaping at least one component of the implant to fit the space shape, and inserting the custom designed implant into the space.

Also in accordance with the present invention, an intervertebral implant of the type having opposed endplates adapted to engage adjacent vertebral surfaces is provided. The implant has at least one component which is custom made to have a shape such that the implant matches a specific intervertebral space into which the implant is to be inserted.

In one embodiment, the component which is custom made is an exterior surface of one of the endplates, so that this surface is customized to fit an irregular shaped intervertebral space. In another embodiment, the component which is custom made is an inlay which is attached to an interior surface of one of the endplates, so that the inlay is customized to fit the implant into an irregular shaped intervertebral space.

It will be appreciated that the method for customizing an intervertebral implant is capable of compensating for the deformity in more than one plane.

It is an object of the present invention to treat an abnormal vertebra having a deformity without requiring removal of the abnormal but otherwise usable vertebra and without resorting to fusion of the abnormal vertebra. Instead, an intervertebral implant is customized to fit against the abnormal surface of the abnormal vertebra in a manner which compensates for the deformity caused by the abnormal vertebra.

It is also an object of the present invention to provide a custom designed universal implant for treatment of an abnormal vertebra.

It is also an object of the present invention to retain relatively full spinal mobility despite the damage or malformation of a vertebra.

Other features and objects of the present invention are stated in or apparent from detailed descriptions of presently preferred embodiments of the invention found hereinbelow.

BRIEF DESCRIPTION OF THE SEVERAL VIEWS OF THE DRAWINGS

FIGS. 6a-d depict a trial implant in a) a front, top and left side perspective view, b) a front view, c) a left side view and d) a front, top and left side perspective view and with a vertebra surface cutting tool therein.

FIG. 7 is a schematic representation of the apparatus used in making the customized implant.

DETAILED DESCRIPTION OF THE INVENTION

As noted above, the present invention is useful with either a damaged vertebra or, where appropriate or where a disc replacement is otherwise being made, with malformed vertebra. Where the present invention is used with malformed vertebrae, it will be appreciated that there will be a targeted vertebra whose abnormality is being compensated for or two adjacent targeted vertebra whose common disc is being replaced. While the targeted vertebra (or adjacent vertebrae) may contribute only to a part of the overall deformed curvature as in scoliosis, correction of that vertebra (or vertebrae) may be desired to reduce the overall curvature and achieve a meaningful improvement in the undesired curvature. In such a case, the targeted vertebra or both targeted vertebrae on either side of the disc being replaced may be overcompensated for in order to help correct the undesired curvature of the adjacent vertebra. For convenience, this overcompensation will still be referred to as "natural" even though it is beyond what would be the compensation to the "natural" surface location of a damaged vertebra which would not have adjacent vertebrae contributing to the curvature.

Figure 1A:
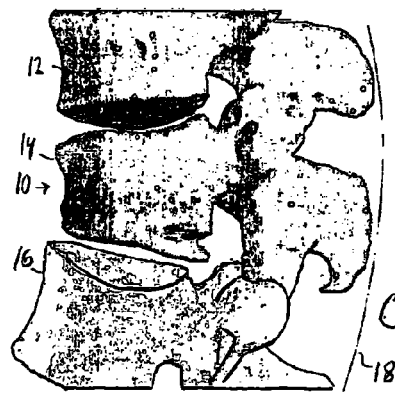
FIGS. 1a, 1b and 1c are, respectively, a left side, a front, and a front, top and left side perspective view of a series of vertebrae including a middle abnormal vertebra which results in a deformity of the series.
Figure 1B:
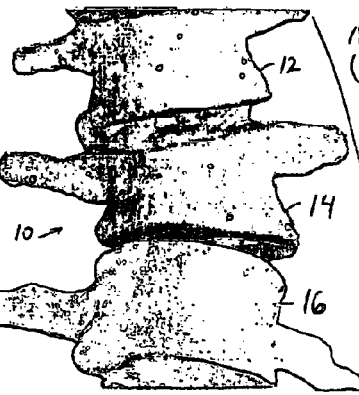
Figure 1C:
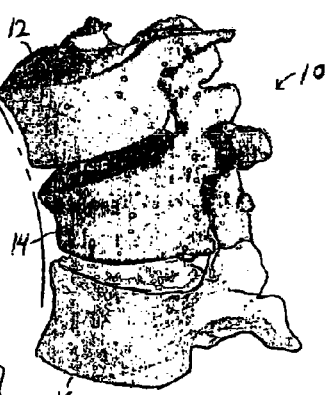

With reference now to the drawings in which like numerals represent like elements throughout the views, there is depicted in FIGS. 1a, 1b and 1c different views of a series 10 of vertebrae 12, 14 and 16. In series 10, vertebra 14 has been damaged and hence is abnormal due to trauma or the like. Thus, hereafter the vertebra in series 10 will be referred to as abnormal vertebra 14, superior (to vertebra 14) vertebra 12 and inferior (to vertebra 14) vertebra 16. The damage and resultant malformation of abnormal vertebra 14 causes series 10 to be compressed and deformed, as shown by the curves of axes 18a, 18b and 18c in the FIGS. 1a-c. It is this deformity which the present invention is designed to compensate for while retaining abnormal vertebra 14 in place.

In accordance with the present invention, in order to compensate for the curvature of series 10, a 3D anatomy of series 10 is obtained. This is simply and conveniently done with a CT scanning device 60 or the like (see FIG. 6), with slices smaller than 1 mm preferred, and optimally between 0.2-1 mm. A high resolution for the slices is required since the deformity of abnormal vertebra 14 must be determined from the CT scan slices. It will be appreciated that the 3D anatomy of all three vertebra of series 10 is required since the proper positioning of abnormal vertebra 14 must also be determined using the obtained 3D anatomy. It will be appreciated that other scanning devices besides a CT scanning device can be used so long as they produce a three dimensional anatomy or the like of the series 10.

Figure 2A:
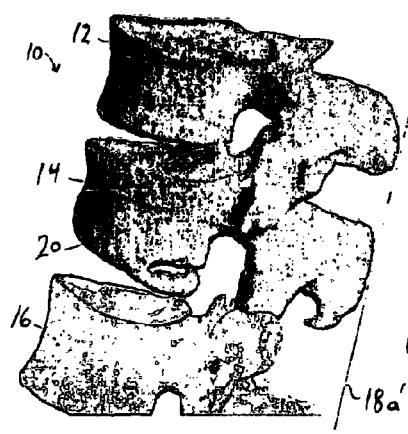
FIGS. 2a, 2b and 2c are, respectively, a left side, a front, and a front, top and left side perspective view of the series of vertebrae including a abnormal vertebra of FIG. 1, but which have been repositioned to correct for the deformity.
Figure 2B:
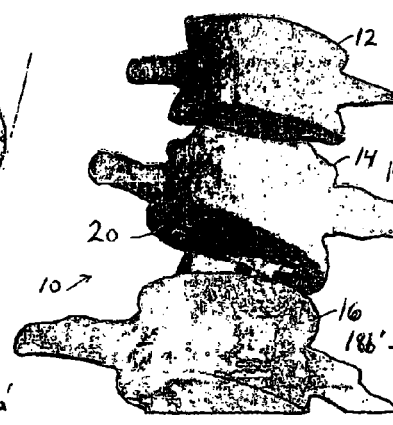

With the 3D anatomy of series 10 obtained and loaded into a computer 62, the 3D anatomy are depicted in a suitable screen 64 or the like as by the appearances of FIG. 1. Next, the user (surgeon) is able using standard software typical in the art to reposition each vertebra of series 10 so that vertebrae 12, 14 and 16 are returned to their natural or desired (including for scoliosis, overcompensated for) positions and/or orientations, that is with axes 18a', 18b' and 18c' now straight lines. With such a repositioned 3D anatomy, the user is able to determine (see) what surface of abnormal vertebra 14 has been abnormal and is causing the deformity (or for scoliosis, how far the two surfaces adjacent to the disc to be replaced should be moved). In this example, it is inferior surface 20 of abnormal vertebra 14 which has been damaged, as best shown in FIG. 2b.

Again using standard software typical in the art, the user is then able to determine where a desired surface 20' of abnormal vertebra 14 would be if vertebra 14 were not damaged. The software then also determines an approximate gap between abnormal surface 20 and a desired surface 20'. With this gap determined, an intervertebral implant 30 is constructed. The construction advantageously takes places by downloading or transferring of data from computer 62 with suitable software to a CAD/CAM milling machine 66 or the like. It will be appreciated that the abnormal surface 20 is preferably smoothed somewhat in the computer before the gap is determined. This smoothing is performed because an exact match of abnormal surface with every (small) peak and valley of the abnormal is not needed; and to some extent, the smoothing will be dependent on the milling machine which is used and the degree of matching attainable with the milling process.

Figure 2C:
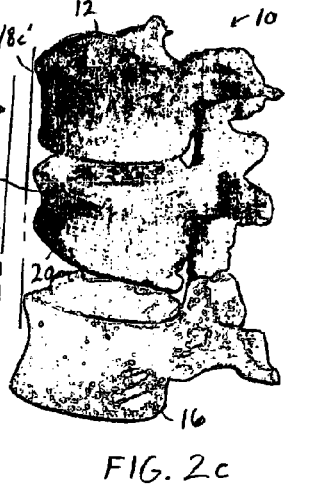
Figure 3A:
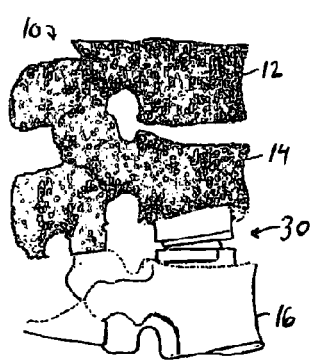
FIGS. 3a, 3b, and 3c are, respectively, a right side, a front, and a left side view of the series of vertebrae including the abnormal vertebra of FIG. 1, but which now have a customized intervertebral implant in accordance with the present invention in the series which customized implant compensates for the deformity.
Figure 3B:
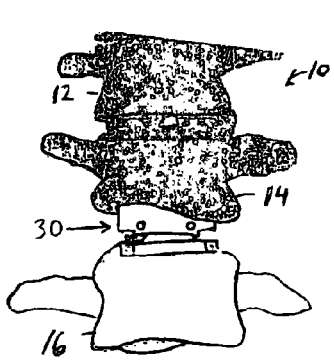
Figure 3C:
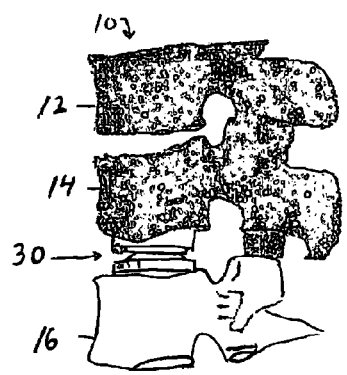

Implant 30 is shown in position in series 10 in FIGS. 3*a-c*. In accordance with the present invention, implant 30 is preferably of the type which allows relative movement between opposed endplates 32 and 34, and hence relative movement of the adjacent vertebrae, as shown in the above identified published applications. As such, the present invention not only provides a customized treatment for abnormal vertebrae, but does so in a manner which allows relative movement between the abnormal vertebra and the adjacent vertebra on the opposite side of the intervertebral space in which implant 30 is inserted. Instruments for insertion of the implant are also shown in the above referenced published applications. It will be appreciated that implant 30 has replaced the disc (not shown, and typically damaged as well) between abnormal vertebra 14 and inferior vertebra 16. Implant 30 is constructed so that the desired (straight) axes 18' shown in FIG. 2 are maintained after implantation of implant 30.

Prior to insertion of the implant 30, it is necessary to utilize a trial implant 70 to guarantee creation of keel grooves in the two vertebrae adjacent implant 30. Trial implants suitable for this purpose are shown in the above identified published application No. 2004/0215198. FIGS. 6*a-c* show this type of trial implant 70, but after being formed to the custom shape using the features of the present invention, in order to fit into the intervertebral space. To properly cut the grooves in the adjacent vertebrae in which the keels of the implant 30 are then secured, a tool 72 is used which is constructed as shown in published application No. 2004/021519. Tool 72 has a suitably angled base end which fits into and is oriented by angled reception slot 74.

Figure 4A:
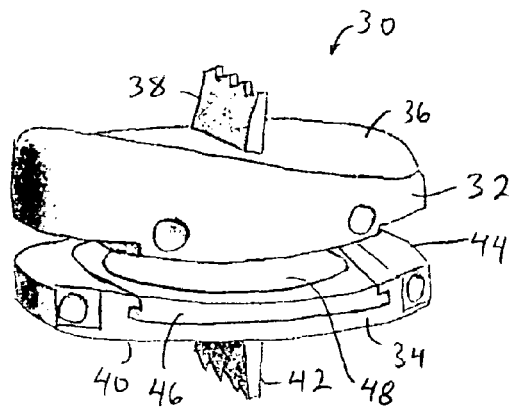
FIGS. 4a and 4b are, respectively, a front, top and left side and a front, top and right side perspective view of the customized implant depicted in FIG. 3.
Figure 4B:
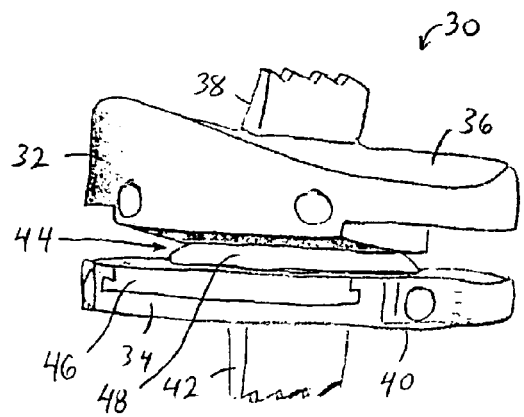

In this embodiment of the present invention, implant 30, which is of the type which allows relative universal movement between the endplates, is customized as shown in FIG. 4. In particular, it will be appreciated that implant 30 (see the above referenced published applications for further details of implant 30 as well as similar implant 50' in FIG. 5) is constructed of a superior endplate 32 and an inferior endplate 34. Superior endplate 32 has an upper vertebral surface engaging surface 36 which is designed to engage abnormal surface 20 and be secured thereto via keel 38. Likewise, inferior endplate 34 has a lower vertebral surface engaging surface 40 which is designed to engage normal surface 22 of inferior vertebra 16 and be secured thereto via keel 42. Provided between endplates 32 and 34 is a suitable articulation, such as a universal joint 44. In this preferred embodiment, universal joint 44 is formed by: a) an inlay 46 having a convex upper surface 48, where inlay 46 is securely received in inferior endplate 34; and b) a mating concave lower surface 50 (not seen, but shown in published application 2005/0085917) formed in superior endplate 34.

If there were no deformity resulting from vertebra 14, so that only the disc between vertebra 14 and 16 were being replaced with implant 30, superior endplate 32 would have a constant thickness or height like that of inferior endplate 34. However, as there has been damage to vertebra 14 so that there is a gap between the location of abnormal surface 20 of vertebra 14 and the desired surface 20' of vertebra 14, it will be seen in FIG. 4 that upper surface 36 of superior endplate 32 has been built up appropriately to fill this gap. Thus, as shown in FIG. 3, with implant 30 in place between vertebrae 14 and 16, no gap exists between abnormal surface 20 and upper surface 36.

It will be appreciated that the build up of upper surface 36 has occurred over most of upper surface 36 thereof, starting from the right (as viewed) and building up to the left as well as back to front. Thus, built up upper surface 36 is not necessarily planar, or even angled in any one plane; rather it may be undulating, or as shown in FIG. 4, built up left to right as well as back to front with some curvature therealong. As a result, the deformity of abnormal vertebra 14 is compensated for in more than one plane in this depicted embodiment.

Figure 5:
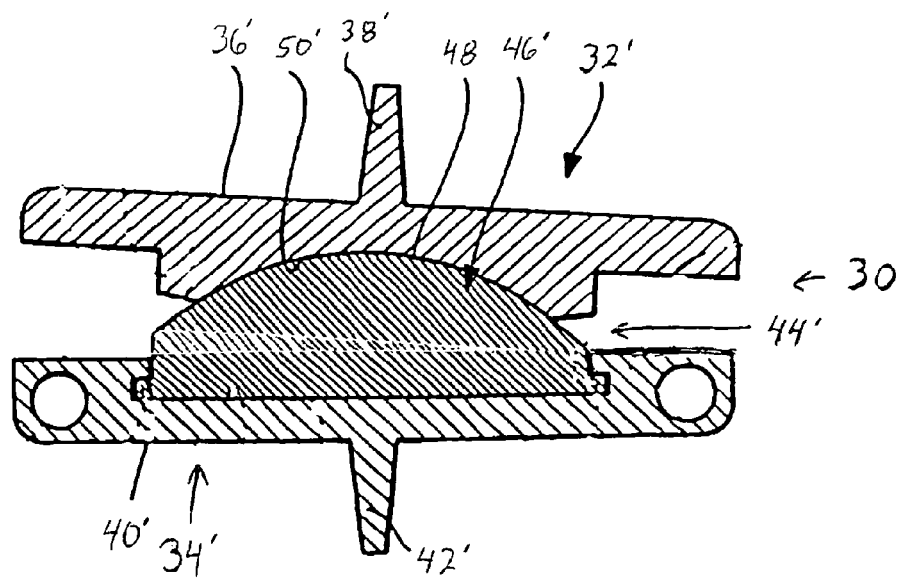
FIG. 5 is a front sectional view of an alternative customized implant in accordance with the present invention.

Depicted in FIG. 5 is a second embodiment of an implant 30' which has been customized in accordance with the present invention. Implant 30' is broadly similar to implant 30 described above, and thus the same identifying numbers but with a prime (') thereafter will be used for the same or similar elements. It will be appreciated that implant 30' is designed for use with an abnormal vertebra having an abnormal superior surface, which in the first embodiment would have occasioned a customized lower vertebral surface engaging surface 40. However, in this embodiment, neither lower vertebral surface engaging surface 40' nor upper vertebral surface engaging surface 36' have been customized. Rather, inlay 46' has been customized so that one side, the left side as viewed, is higher (has a greater thickness) than the right side. This higher left side causes, upon implantation, lower vertebral surface engaging surface 40' to be angled as shown to compensate for the damage to the adjacent vertebral superior surface when the universal joint 44' is at the neutral or centered position (which is shown in FIG. 5).

As inlay 46' is the element which provides the compensation, implant 30' is usable primarily where the abnormal surface of the vertebra is relatively planar. However, where appropriate, the use of a customized inlay may afford some advantages, such as easier and quicker fabrication since inlay 46' is formed of polyethylene.

It will also be appreciated that where a disc between two vertebrae which are malformed as by scoliosis is to be replaced, the adjacent vertebral surfaces will be undamaged and thus implant 30 or 30' is usable. As noted above, implant 30' can be designed to overcompensate for the curvature so that the remaining malformed vertebra are advantageously oriented relative to the implant. In such a case, both endplates of implant 30 could have customized (built up) surfaces, or both the inlay of implant 30' and the other endplate surface 36' could be customized (built up). It will further be appreciated that besides building up inlay 46, or in addition thereto, the opposite facing surface of endplate 32 could be built up in the same manner as inlay 46.

It is anticipated that the methods described above can be accomplished relatively quickly and easily. Thus, such a method could even be performed while surgery is underway to repair a trauma. Once the 3D anatomy scan is made, the CAD/CAM machine would be immediately directed to make the needed customized implant part from a stock of parts ready to be milled.

While the present invention has been described with respect to exemplary embodiments thereof, it will be understood by those of ordinary skill in the art that variations and modifications can be effected within the scope and spirit of the invention.

We claim:

1. A method for customizing an intervertebral implant to be implanted in a series of vertebrae, the series of vertebrae including an abnormal vertebra, a vertebra superior to the abnormal vertebra, and a vertebra inferior to the abnormal vertebrae, where the series of vertebrae has a deformed curvature in comparison to a known natural curvature of the series of vertebrae, said method comprising the steps of:
   a) obtaining a 3D anatomy of the series of vertebrae in a computer;
   b) repositioning of the abnormal, superior and inferior vertebrae of the 3D anatomy of the series of vertebrae in the computer to eliminate the deformed curvature of the series of the vertebrae so as to arrange the series of vertebrae in the natural curvature;
   c) determining whether a superior or inferior surface of the abnormal vertebra is an abnormal surface causing the deformed curvature of the series of vertebrae;
   d) determining an approximate gap between the abnormal surface of the abnormal vertebra and a desired surface of the abnormal vertebra;
   e) custom constructing a trial implant to engage the abnormal surface and to fill the determined approximate gap, whereby implantation of the trial implant between the abnormal surface of the abnormal vertebra and adjacent surface of one of the superior and inferior vertebrae of the series vertebrae results in the series of vertebrae being arranged in the natural curvature,
   said custom constructing of the trial implant step including the step of providing, on surface of the trial implant which respectively engage the abnormal surface and the adjacent surface, slots therein for reception of a cutting tool used to cut keel grooves in the abnormal surface and the adjacent surface; and
   f) custom constructing the intervertebral implant to engage the abnormal surface and to fill the determined approximate gap, the intervertebral implant including a superior endplate and an inferior endplate, the custom constructing the intervertebral implant step including building up one of the inferior and superior endplates that abuts the abnormal vertebra, such that at least a portion of the built up endplate has a thickness greater than a corresponding portion of the other endplate, whereby implantation of the intervertebral implant between the abnormal surface and the adjacent surface likewise results in the series of vertebrae being arranged in the natural curvature,
   said custom constructing of the intervertebral implant step including the step of providing, on the endplates of the intervertebral implant which respectively engage the abnormal surface and the adjacent surface, keels extending therefrom which are to be received in the keel grooves.

2. The method for customizing the intervertebral implant as claimed in claim 1, wherein said constructing step e) includes constructing an engaging surface of the trial implant with a height which will engage the abnormal surface and fill the determined gap, and wherein said constructing step f) includes constructing an engaging surface of the intervertebral implant with a height which will engage the abnormal surface and fill the determined gap.

3. The method for customizing the intervertebral implant as claimed in claim 1, wherein the intervertebral implant includes an endplate and an inlay received in the endplate; and wherein said constructing step f) includes constructing of the inlay with a height which will cause an engaging surface of the endplate to engage the abnormal surface and to fill the determined gap.

4. The method for customizing the intervertebral implant as claimed in claim 1, wherein said constructing step f) includes a further step of smoothing of the abnormal surface of the abnormal vertebra into a smoothed surface in the computer so that an engaging surface of the intervertebral implant is matched to the smoothed surface.

5. The method for customizing the intervertebral implant as claimed in claim 1, wherein said constructing step f) further includes a step of transferring data from the computer to a CAD/CAM milling machine which forms an engaging surface of the intervertebral implant.

6. The method for customizing the intervertebral implant as claimed in claim 1, wherein the repositioning step b) includes the step of compensating for the deformed curvature in more than one plane.

7. The method for customizing an intervertebral implant as claimed in claim 1, wherein the step (f) comprises the step of building up the superior endplate.

8. The method for customizing an intervertebral implant as claimed in claim 1, wherein the step (f) comprises the step of building up the inferior endplate.

9. A method for customizing an intervertebral implant to be implanted between an abnormal surface of an abnormal vertebra and an adjacent surface of an adjacent superior or inferior vertebra in a series of vertebrae including the abnormal vertebra, the superior vertebra and the inferior vertebra where the series of vertebrae has deformed curvature, and where the intervertebral implant includes an engages surface which engages the abnormal surface of the abnormal vertebra, said method comprising the steps of:
   a) obtaining a 3D anatomy of the series of vertebrae in a computer which shows the deformed curvature;
   b) repositioning the 3D anatomy of the abnormal vertebra, the superior vertebrae, and the interior vertebra of the series of vertebrae with the computer as needed to arrange the series of vertebrae in a known natural curvature;
   c) determining with the repositioned 3D anatomy of the series of vertebrae whether a superior or inferior surface of the abnormal vertebra is the abnormal surface causing the deformed curvature;
   d) constructing an engaging surface of a trial implant to match the abnormal surface of the abnormal vertebra in the repositioned 3D anatomy while an opposite surface of the trial implant matches the adjacent surface of the one of the superior and inferior vertebrae, whereby implantation of the trial implant between the abnormal surface of the abnormal vertebra and the adjacent surface of the one of the superior and inferior vertebrae results in the series of vertebrae being arranged in the natural curvature,
   said constructing of the engaging surface of the trial implant step including the step of providing, on the engaging and opposite surfaces of the trial implant which respectively engage the abnormal surface and the adjacent surface, slots therein for reception of a cutting tool used to cut keel grooves in the abnormal surface and the adjacent surface; and
   e) constructing an engaging surface of the intervertebral implant to match the abnormal surface in repositioned 3D anatomy while an opposite surface of the intervertebral implant matches the adjacent surface, the intervertebral implant including a superior endplate and an inferior endplate, the custom constructing the engaging surface step including building up one of the inferior and superior endplates that abuts the abnormal vertebra, such that at least a portion of the built up endplate has a thickness greater than a corresponding portion of the other endplate, whereby implantation of the intervertebral implant between the abnormal surface and the adjacent surface likewise results in the series of vertebrae being arranged in the natural curvature, said constructing the engaging surface of the intervertebral implant step including the step of providing, on the engaging and opposite surface of the intervertebral implant which respectively engage the abnormal surface and the adjacent surface, keels extending therefrom which are to be received in the keel grooves.

10. The method for customizing the intervertebral implant as claimed in claim 9, wherein said constructing step e) includes a step of smoothing of the abnormal surface of the abnormal vertebra in the computer to define a smoothed surface so that the engaging surface of the intervertebral implant is matched to the smoothed surface.

11. The method for customizing the intervertebral implant as claimed in claim 9, wherein said constructing step e) further includes a step of transferring data from the computer to a CAD/CAM milling machine which forms the engaging surface of the intervertebral implant.

12. The method for customizing the intervertebral implant as claimed in claim 9, wherein the repositioning step b) includes the step of compensating for the deformed curvature in more than one plane.

13. The method for customizing the intervertebral implant as claimed in claim 9, wherein step (e) comprises the step of building up the inferior endplate.

14. The method for customizing the intervertebral implant as claimed in claim 9, wherein step (e) comprises the step of building up the inferior endplate.

15. A method for providing a custom designed intervertebral implant for insertion into an irregularly shaped intervertebral space causing a deformed curvature of a series of vertebrae including an abnormal vertebra, comprising the steps of:
   a) determining a shape of the irregular intervertebral space, wherein said determining step includes the steps of:
      i) obtaining of a 3D anatomy of the series of vertebrae including the abnormal vertebra and a superior vertebra and an inferior vertebra of the abnormal vertebra,
      ii) repositioning of each vertebra of the 3D anatomy of the series of the vertebrae in the computer as needed to eliminate the deformed curvature of the series of vertebrae caused by the abnormal vertebra so as to arrange the series of vertebrae into a known natural curvature, and
      iii) determining an approximate gap between an abnormal surface of the abnormal vertebra when the abnormal vertebrae is causing the deformed curvature and a desired surface of the abnormal vertebra when the abnormal vertebrae is positioned in the known natural curvature;
   b) custom designing a trial implant to match opposing vertebral surfaces of the irregular intervertebral space, which opposing vertebral surfaces include the abnormal surface of the abnormal vertebra and an adjacent surface of an adjacent one of the superior or inferior vertebrae, and additionally to fill the determined approximate gap, said custom designing of the trial implant step including the step of providing, on engaging and opposite surfaces of the trial implant which respectively engage the abnormal surface and the adjacent surface, slots therein for reception of a cutting tool used to cut keel grooves in the abnormal surface and the adjacent surface;
   c) inserting the custom designed trial implant into the intervertebral space such that the custom designed trial implant essentially fills the intervertebral space and thereby arranges the series of vertebrae in the natural curvature so that the keel grooves can be cut;
   d) custom designing the intervertebral implant to match opposing abnormal and adjacent surfaces of the irregular intervertebral space and additionally to fill the determined approximate gap, said custom designing of the intervertebral implant step including the step of providing, on engaging and opposite surface of the intervertebral implant which respectively engage the abnormal surface and the adjacent surface, keels extending therefrom which are to be received in the keel grooves, the intervertebral implant including a superior endplate and an inferior endplate, the custom designing of the intervertebral implant step further including building up one of the engaging and opposite surfaces that abuts the abnormal vertebra, such that at least a portion of the built up endplate has a thickness greater than a corresponding portion of the endplate; and
   e) inserting the custom designed intervertebral implant into the intervertebral space such that i) the custom designed intervertebral implant essentially fills the intervertebral space and thereby arranges the series of vertebrae in the natural curvature, and ii) the keels are received in the slots.

16. The method for providing the custom designed intervertebral implant as claimed in claim 15, wherein the custom designed intervertebral implant is of an articulated type.

17. The method for providing the custom designed intervertebral implant as claimed in claim 15, wherein said designing step d) includes constructing an engaging surface of the intervertebral implant such that the intervertebral implant has a height that fills the approximate gap.

18. The method for providing the custom designed intervertebral implant as claimed in claim 15, wherein said designing step d) includes matching the custom designed intervertebral implant to a smoothed surface of the intervertebral space.

19. The method for providing the custom designed intervertebral implant as claimed in claim 15, wherein the custom designed intervertebral implant compensates for the irregularly shaped intervertebral space in more than one plane.

20. The method for providing the custom designed intervertebral implant as claimed in claim 15, wherein step (d) comprises the step of building up the superior endplate.

21. The method for providing the custom designed intervertebral implant as claimed in claim 15, wherein step (d) comprises the step of building up the inferior endplate.

* * * * *